United States Patent
Ogawa

(10) Patent No.: US 12,238,436 B2
(45) Date of Patent: Feb. 25, 2025

(54) IMAGING DEVICE, ENDOSCOPE SYSTEM, AND IMAGING METHOD

(71) Applicant: OLYMPUS MEDICAL SYSTEMS CORP., Hachioji (JP)

(72) Inventor: Keisuke Ogawa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 165 days.

(21) Appl. No.: 18/189,522

(22) Filed: Mar. 24, 2023

(65) Prior Publication Data
US 2023/0232131 A1    Jul. 20, 2023

Related U.S. Application Data

(63) Continuation of application No. PCT/JP2020/036516, filed on Sep. 28, 2020.

(51) Int. Cl.
| | |
|---|---|
| *H04N 25/709* | (2023.01) |
| *A61B 1/00* | (2006.01) |
| *A61B 1/045* | (2006.01) |
| *A61B 1/05* | (2006.01) |

(52) U.S. Cl.
CPC ....... *H04N 25/709* (2023.01); *A61B 1/00009* (2013.01); *A61B 1/045* (2013.01); *A61B 1/05* (2013.01)

(58) Field of Classification Search
CPC .. H04N 25/709; H04N 25/76; A61B 1/00009; A61B 1/045; A61B 1/05; A61B 1/00006; A61B 1/00027
See application file for complete search history.

(56) References Cited

U.S. PATENT DOCUMENTS

| | | | |
|---|---|---|---|
| 6,468,201 B1* | 10/2002 | Burdick | .................... H03F 3/19 |
| | | | 600/109 |
| 2015/0280550 A1 | 10/2015 | Minakuchi | |
| 2017/0041561 A1* | 2/2017 | Akahane | .............. H04N 25/709 |
| 2018/0199003 A1* | 7/2018 | Shigehisa | .............. H04N 25/76 |
| 2019/0350447 A1 | 11/2019 | Kato | |
| 2021/0102844 A1* | 4/2021 | Chan | ......................... G01J 1/46 |
| 2022/0165767 A1* | 5/2022 | Fujii | ..................... H01L 21/768 |

FOREIGN PATENT DOCUMENTS

| | | |
|---|---|---|
| EP | 3205256 A1 | 8/2017 |
| JP | 2011-206333 A | 10/2011 |
| JP | 2015-192696 A | 11/2015 |
| WO | 2018/167912 A1 | 9/2018 |

OTHER PUBLICATIONS

International Search Report dated Dec. 15, 2020, issued in counterpart Application No. PCT/JP2020/036516 with English translation. (4 pages).

* cited by examiner

*Primary Examiner* — Timothy R Newlin
(74) *Attorney, Agent, or Firm* — WHDA, LLP

(57) ABSTRACT

An imaging device includes a camera unit and a control unit. A first power source voltage is transferred from the control unit to the camera unit by a power source line and is input into the camera unit as a second power source voltage. The camera unit is configured to output a video signal, a reference signal having a reference voltage, and a voltage signal in accordance with the second power source voltage to a video signal line. The control unit is configured to measure a voltage value of each of the reference signal and the voltage signal. The control unit is configured to calculate a control value of the first power source voltage by using the measured voltage value.

9 Claims, 7 Drawing Sheets

IMAGING DEVICE, ENDOSCOPE SYSTEM, AND IMAGING METHOD

The present application is a continuation application based on International Patent Application No. PCT/JP2020/036516 filed on Sep. 28, 2020, the content of which is incorporated herein by reference.

BACKGROUND OF THE INVENTION

Field of the Invention

The present invention relates to an imaging device, an endoscope system, and an imaging method.

DESCRIPTION OF RELATED ART

An endoscope system includes an endoscope (camera unit) and a main body, and the endoscope and the main body are connected to each other by a cable. An imager is mounted in the distal end of the endoscope. A power source voltage used for driving the imager is transferred from the main body to the distal end of the endoscope via the cable. Hereinafter, the power source voltage that has reached the distal end of the endoscope will be called a distal end voltage.

The power source voltage needs to be adjusted such that the distal end voltage has an appropriate value in order to drive the imager stably. However, the value of the distal end voltage may be less or greater than a voltage value recommended as an operation voltage value of the imager due to factors such as the length of the cable, deviations of the characteristics of the cable, and fluctuations of a current used for driving the imager. Hereinafter, the voltage value recommended as the operation voltage value of the imager will be called a recommended voltage value. As a result, problems may occur in driving the imager stably.

The prior art has improved the accuracy of circuit components or has performed an individual inspection of a power source at the time of production by considering a voltage drop caused by a cable and by considering fluctuations of current consumption caused by a change of a load of an imager in order to restrict the value of the distal end voltage within the recommended voltage value. Thus, the prior art has improved the accuracy of a power source voltage. However, in recent years, the diameter of a power source cable has needed to be reduced because of the demand for further reducing the diameter of an endoscope, and the distal end voltage is likely to be affected by the fluctuations of current consumption caused by the change of the load of the imager. Therefore, it has become difficult to restrict the value of the distal end voltage within the recommended voltage value.

A technique disclosed in Japanese Unexamined Patent Application, First Publication No. 2011-206333 provides a function of adjusting a power source voltage based on the distal end voltage. According to the technique, the distal end voltage is monitored at all times by using a dedicated cable for determining the distal end voltage, and the power source voltage is adjusted such that the distal end voltage has an appropriate value.

SUMMARY OF THE INVENTION

According to a first aspect of the present invention, an imaging device includes a camera unit and a control unit. The camera unit includes an image sensor, a reference voltage generation circuit, and a signal output circuit. The image sensor is configured to receive a first power source voltage transferred by a power source line as a second power source voltage and generate a video signal by using the second power source voltage. The reference voltage generation circuit is configured to generate a first reference voltage. The signal output circuit is configured to output the video signal, a reference signal having the first reference voltage, and a voltage signal having a first voltage indicating the second power source voltage to a video signal line. The control unit includes a signal reception circuit, a calculation circuit, a power source voltage generation circuit, and a voltage adjustment circuit. The signal reception circuit is configured to receive the video signal transferred by the video signal line, the reference signal having a second reference voltage, and the voltage signal having a second voltage and measure a value of the second reference voltage and a value of the second voltage. The received reference signal has the second reference voltage that has changed from the first reference voltage. The received voltage signal has the second voltage that has changed from the first voltage. The calculation circuit is configured to calculate a control value used for adjusting a value of the first power source voltage by using a value of the first reference voltage, the value of the second reference voltage, and the value of the second voltage. The power source voltage generation circuit is configured to generate the first power source voltage and output the generated first power source voltage to the power source line. The voltage adjustment circuit is configured to adjust the value of the first power source voltage by controlling the power source voltage generation circuit based on the control value.

According to a second aspect of the present invention, in the first aspect, the control unit may further include a current measurement circuit configured to measure a value of a current that flows through the power source line. The calculation circuit may be configured to calculate a resistance value of the power source line by using the value of the first power source voltage, the value of the first reference voltage, and the value of the current and calculate the control value by using the resistance value when the value of the second voltage is the same as the value of the second reference voltage.

According to a third aspect of the present invention, in the second aspect, a value of the second power source voltage is not necessarily within a range of a voltage of the video signal. The camera unit may further include a conversion circuit configured to convert the second power source voltage into the first voltage having a value within the range so as to generate the voltage signal. The calculation circuit may be configured to calculate the resistance value by using the value of the first power source voltage, the value of the first reference voltage, the value of the current, and a value indicating a ratio of the value of the second power source voltage to the value of the first voltage.

According to a fourth aspect of the present invention, in the first aspect, the calculation circuit may be configured to calculate a value of the second power source voltage corresponding to the first voltage by using the value of the first reference voltage, the value of the second reference voltage, and the value of the second voltage and calculate the control value by using the value of the second power source voltage.

According to a fifth aspect of the present invention, in the fourth aspect, a value of the second power source voltage is not necessarily within a range of a voltage of the video signal. The camera unit may further include a conversion circuit configured to convert the second power source voltage into the first voltage having a value within the range so as to generate the voltage signal. The calculation circuit may be configured to calculate the value of the second power source voltage by using the value of the first reference voltage, the value of the second reference voltage, the value of the second voltage, and a value indicating a ratio of the value of the second power source voltage to the value of the first voltage.

According to a sixth aspect of the present invention, in the fifth aspect, the control unit may further include a current measurement circuit configured to measure a value of a current that flows through the power source line. The calculation circuit may be configured to calculate a resistance value of the power source line by using the value of the first power source voltage, the value of the second power source voltage, and the value of the current and calculate the control value by using the resistance value.

According to a seventh aspect of the present invention, in the first aspect, the signal output circuit may be configured to output the video signal to the video signal line in a first period, output the reference signal to the video signal line in a second period different from the first period, and output the voltage signal to the video signal line in a third period different from any of the first period and the second period.

According to an eighth aspect of the present invention, an endoscope system includes a scope and the imaging device. The scope has a distal end and is to be inserted into a living body. The camera unit is disposed in the distal end.

According to a ninth aspect of the present invention, an imaging method is provided. The method includes receiving a first power source voltage transferred by a power source line as a second power source voltage; generating a video signal by using the second power source voltage; generating a first reference voltage; outputting the video signal, a reference signal having the first reference voltage, and a voltage signal having a first voltage indicating the second power source voltage to a video signal line; and receiving the video signal transferred by the video signal line, the reference signal having a second reference voltage, and the voltage signal having a second voltage. The received reference signal has the second reference voltage that has changed from the first reference voltage. The received voltage signal has the second voltage that has changed from the first voltage. The method includes measuring a value of the second reference voltage and a value of the second voltage; calculating a control value used for adjusting a value of the first power source voltage by using a value of the first reference voltage, the value of the second reference voltage, and the value of the second voltage; generating the first power source voltage; outputting the generated first power source voltage to the power source line; and adjusting the value of the first power source voltage by controlling a power source voltage generation circuit based on the control value.

DETAILED DESCRIPTION OF THE INVENTION

Hereinafter, embodiments of the present invention will be described with reference to the drawings. Each of the embodiments will be described in detail by using an endoscope system as an example of an imaging device.

First Embodiment

Figure 1:
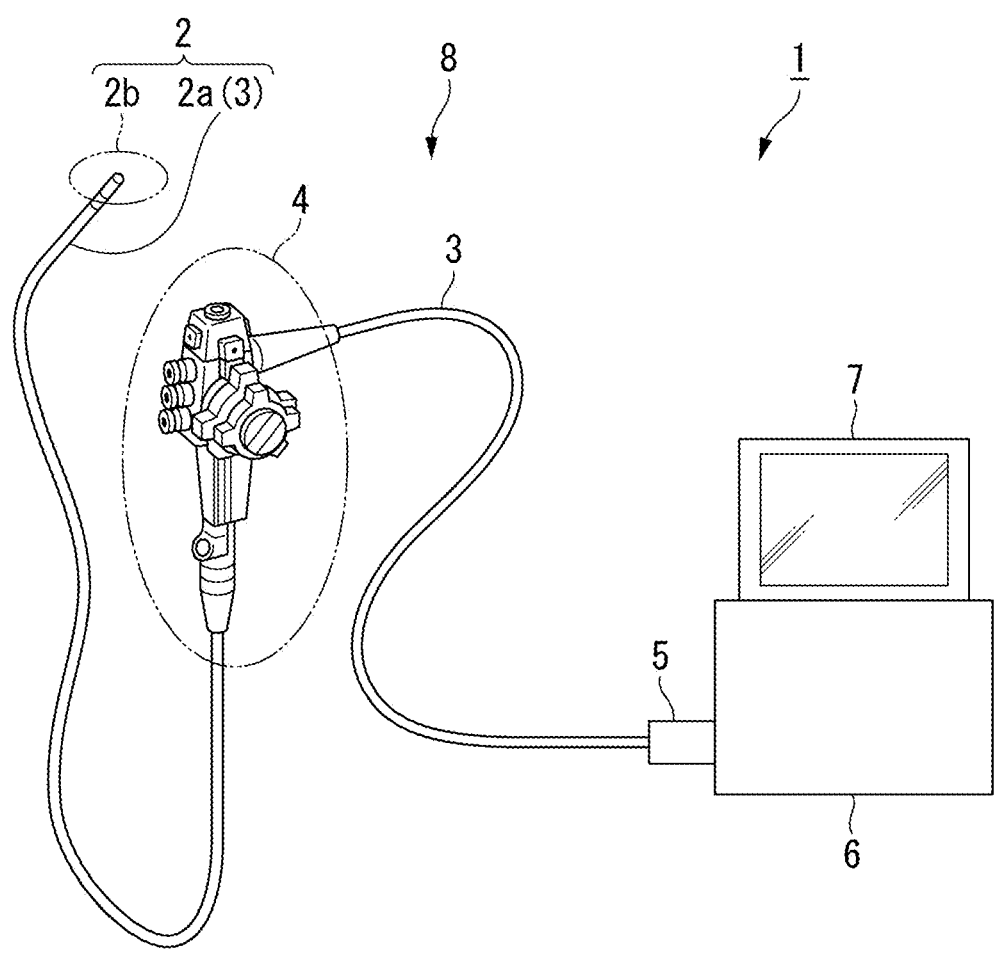
FIG. 1 is a schematic diagram showing a configuration of an endoscope system according to a first embodiment of the present invention.

FIG. 1 shows a configuration of an endoscope system 1 according to a first embodiment of the present invention. The endoscope system 1 shown in FIG. 1 includes an endoscope insertion unit 2, a transmission cable 3, an operation unit 4, a connector unit 5, a processor 6, and a display device 7. The endoscope insertion unit 2, the transmission cable 3, the operation unit 4, and the connector unit 5 constitute a scope.

Figure 2:
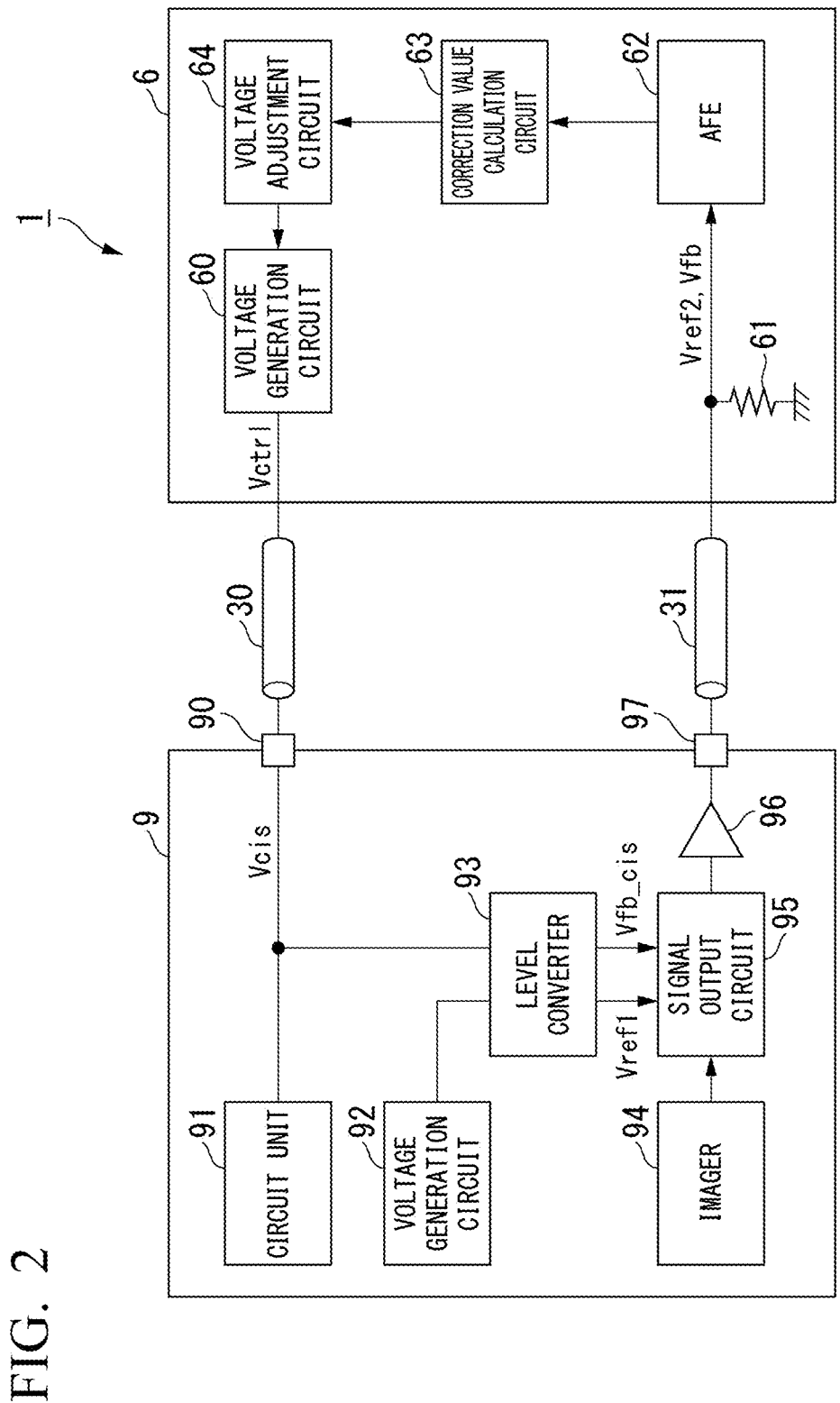
FIG. 2 is a block diagram showing a configuration of the endoscope system according to the first embodiment of the present invention.

The endoscope insertion unit 2 includes an insertion unit 2a. The insertion unit 2a is part of the transmission cable 3. The insertion unit 2a is to be inserted inside a living body, which is a subject. The endoscope insertion unit 2 generates a video signal by imaging the inside of the subject. The endoscope insertion unit 2 outputs the generated video signal to the processor 6. A camera unit 9 shown in FIG. 2 is disposed in a distal end 2b of the insertion unit 2a. In the insertion unit 2a, the operation unit 4 is connected to the end part opposite the distal end 2b. The operation unit 4 receives various operations for the endoscope insertion unit 2 from a user.

The transmission cable 3 connects the camera unit 9 and the connector unit 5. The video signal generated by the camera unit 9 is output to the connector unit 5 via the transmission cable 3.

The connector unit 5 is connected to the endoscope insertion unit 2 and the processor 6. The connector unit 5 performs predetermined processing on the video signal output from the endoscope insertion unit 2. The connector unit 5 outputs the video signal to the processor 6.

The processor 6 performs image processing on the video signal output from the connector unit 5. Furthermore, the processor 6 centrally controls the entire endoscope system 1.

The display device 7 displays a video based on the video signal processed by the processor 6. In addition, the display device 7 displays various kinds of information related to the endoscope system 1.

The endoscope system 1 includes a light source device that generates illumination light emitted to the subject. The light source device is not shown in FIG. 1.

FIG. 2 shows an internal configuration of the endoscope system 1. The endoscope system 1 shown in FIG. 2 includes the camera unit 9 and the processor 6. The camera unit 9 is disposed in the distal end 2b of an endoscope. The operation unit 4, the connector unit 5, and the display device 7 are not shown in FIG. 2.

The camera unit 9 includes a power source terminal 90, a circuit unit 91, a voltage generation circuit 92, a level converter 93, an imager 94, a signal output circuit 95, a buffer 96, and a video terminal 97. At least one of the circuit unit 91, the voltage generation circuit 92, the level converter 93, the signal output circuit 95, and the buffer 96 may be disposed in the imager 94.

The processor 6 includes a voltage generation circuit 60, a resistor 61, an analog front end (AFE) 62, a correction value calculation circuit 63, and a voltage adjustment circuit 64. The processor 6 is a control unit. All or part of the configuration of the processor 6 shown in FIG. 2 may be disposed in the operation unit 4 or the connector unit 5.

The transmission cable 3 shown in FIG. 1 includes a power source line 30 and a video signal line 31 shown in FIG. 2.

A schematic configuration of the endoscope system 1 will be described. The camera unit 9 and the processor 6 are connected to each other by both the power source line 30 that transfers a first power source voltage Vctrl and the video signal line 31 that transfers a video signal. The first power source voltage Vctrl transferred by the power source line 30 is input into the camera unit 9 as a second power source voltage Vcis. The imager 94 generates a video signal by using the second power source voltage Vcis. The voltage generation circuit 92 and the level converter 93 (reference voltage generation circuit) generate a first reference voltage Vref1. The signal output circuit 95 outputs the video signal, a reference signal having the first reference voltage Vref1, and a voltage signal having a first voltage Vfb_cis indicating the second power source voltage Vcis to the video signal line 31.

The AFE 62 (signal reception circuit) receives the video signal, a reference signal, and a voltage signal transferred by the video signal line 31. The reference signal has a second reference voltage Vref2 that has changed from the first reference voltage Vref1 by passing through the video signal line 31. The voltage signal has a second voltage Vfb that has changed from the first voltage Vfb_cis by passing through the video signal line 31. The AFE 62 measures a value of the second reference voltage Vref2 and a value of the second voltage Vfb. The correction value calculation circuit 63 (calculation circuit) calculates a control value used for adjusting the value of the first power source voltage Vctrl by using the value of the first reference voltage Vref1, the value of the second reference voltage Vref2, and the value of the second voltage Vfb. The voltage generation circuit 60 (power source voltage generation circuit) generates the first power source voltage Vctrl and outputs the generated first power source voltage Vctrl to the power source line 30. The voltage adjustment circuit 64 adjusts the value of the first power source voltage Vctrl based on the control value calculated by the correction value calculation circuit 63.

A detailed configuration of the endoscope system 1 will be described. For example, the voltage generation circuit 60 is a voltage regulator. The voltage generation circuit 60 generates the first power source voltage Vctrl, which is a direct-current (DC) voltage.

The first power source voltage Vctrl generated by the voltage generation circuit 60 is output to the power source line 30. The power source line 30 is a signal line disposed in the transmission cable 3. The power source line 30 transfers the first power source voltage Vctrl output from the voltage generation circuit 60 to the camera unit 9.

The power source terminal 90 is connected to the power source line 30. The first power source voltage Vctrl transferred by the power source line 30 is input into the power source terminal 90. The power source terminal 90 outputs the first power source voltage Vctrl to each circuit in the camera unit 9 as the second power source voltage Vcis. The second power source voltage Vcis is a power source voltage transferred by the power source line 30 to the camera unit 9 and is a voltage on a path including a path from the power source terminal 90 to the imager 94. A voltage drop is generated due to a DC resistance of the power source line 30, and the second power source voltage Vcis is attenuated. Therefore, the value of the second power source voltage Vcis is less than that of the first power source voltage Vctrl in the processor 6.

The circuit unit 91 includes a circuit such as a timing generator or a phase-locked loop (PLL). The circuit unit 91 operates based on the second power source voltage Vcis.

The voltage generation circuit 92 and the level converter 93 constitute a reference voltage generation circuit. The voltage generation circuit 92 generates a first reference voltage based on the second power source voltage Vcis. For example, the voltage generation circuit 92 is constituted by a bandgap reference and can generate a voltage having a stable value.

The value of the second power source voltage Vcis is not within the range of the voltage of the video signal. The level converter 93 (conversion circuit) converts the second power source voltage Vcis into the first voltage Vfb_cis having a value within the range of the voltage of the video signal, thus generating the voltage signal.

For example, the value of the second power source voltage Vcis is about 3.3 V, and the range of the voltage of the video signal is about 100 mV. The range of the voltage of the video signal is a range from a minimum allowable voltage of the video signal to a maximum allowable voltage of the video signal. In order to fit the value of the second power source voltage Vcis into this range, the level converter 93 converts the second power source voltage Vcis into the first voltage Vfb_cis. The value of the first voltage Vfb_cis is less than that of the second power source voltage Vcis.

The second power source voltage Vcis and the first voltage Vfb_cis meet a condition shown in the following Expression (1). A coefficient k in Expression (1) indicates a ratio of the value of the second power source voltage Vcis to the value of the first voltage Vfb_cis. The coefficient k is a predetermined value greater than 1.

$$Vfb\_cis = Vcis \times 1/k \tag{1}$$

Similarly to the above, the level converter 93 converts the first reference voltage generated by the voltage generation circuit 92 into the first reference voltage Vref1 having a value within the range of the voltage of the video signal, thus generating the reference signal. The level converter 93 outputs both the reference signal having the first reference voltage Vref1 and the voltage signal having the first voltage Vfb_cis to the signal output circuit 95.

The imager 94 is an image sensor such as a complementary metal-oxide semiconductor (CMOS) sensor. The imager 94 includes a plurality of pixels and generates a video signal having a voltage generated based on the second power source voltage Vcis. The imager 94 outputs the video signal to the signal output circuit 95.

The signal output circuit 95 outputs an analog signal output from the imager 94 or the level converter 93 to the video signal line 31 via the buffer 96 and the video terminal 97. The signal output circuit 95 outputs the video signal output from the imager 94 to the video signal line 31 in a first period. The signal output circuit 95 outputs the reference signal output from the level converter 93 to the video signal line 31 in a second period different from the first period. The signal output circuit 95 outputs the voltage signal output from the level converter 93 to the video signal line 31 in a third period different from any of the first period and the second period.

For example, the first period is a period during which the imager 94 outputs the video signal. An entire period of the second period and the third period is all or part of a period excluding the first period. For example, the second period and the third period are included in a blanking period during which the imager 94 stops the output of the video signal. The second period and the third period are one or both of a horizontal blanking period and a vertical blanking period.

Figure 3:
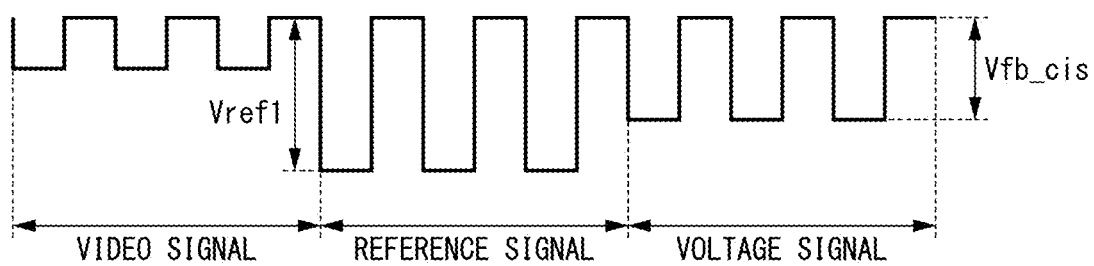
FIG. 3 is a timing chart showing a waveform of each signal output from a signal output circuit included in the endoscope system according to the first embodiment of the present invention.

FIG. 3 shows a waveform of each signal output from the signal output circuit 95. Waveforms of the video signal, the reference signal, and the voltage signal are shown in FIG. 3. The horizontal direction in FIG. 3 indicates time, and the vertical direction in FIG. 3 indicates a voltage value.

The signal output circuit 95 outputs the reference signal having the first reference voltage Vref1 after outputting the video signal. The signal output circuit 95 outputs the voltage signal having the first voltage Vfb_cis after outputting the reference signal.

The order of the reference signal and the voltage signal is not limited to that shown in FIG. 3. The signal output circuit 95 may output the reference signal after outputting the voltage signal.

The analog signal output from the signal output circuit 95 is input into the video terminal 97 via the buffer 96. The video terminal 97 is connected to the video signal line 31. The video terminal 97 sequentially outputs the video signal, the reference signal, and the voltage signal to the video signal line 31. The video signal line 31 is a signal line disposed in the transmission cable 3. The video signal line 31 transfers the video signal to the processor 6 in the first period, transfers the reference signal to the processor 6 in the second period, and transfers the voltage signal to the processor 6 in the third period.

The resistor 61 is connected to the video signal line 31. The resistor 61 is a terminal resistor. The AFE 62 is connected to the video signal line 31. The video signal is input into the AFE 62 in the first period, the reference signal is input into the AFE 62 in the second period, and the voltage signal is input into the AFE 62 in the third period.

Figure 4:
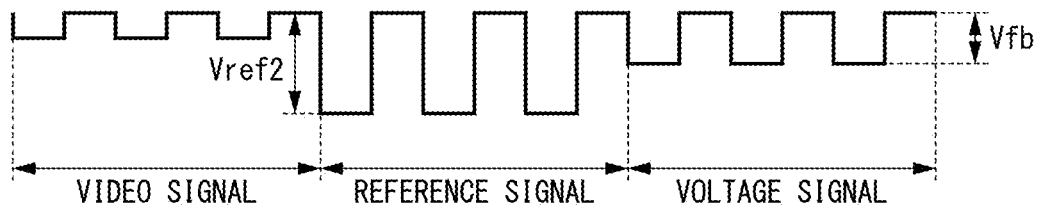
FIG. 4 is a timing chart showing a waveform of each signal received by a signal reception circuit included in the endoscope system according to the first embodiment of the present invention.

FIG. 4 shows a waveform of each signal received by the AFE 62, which is a signal reception circuit. Waveforms of the video signal, the reference signal, and the voltage signal are shown in FIG. 4. The horizontal direction in FIG. 4 indicates time, and the vertical direction in FIG. 4 indicates a voltage value.

The AFE 62 receives the reference signal having the second reference voltage Vref2 after receiving the video signal. The AFE 62 receives the voltage signal having the second voltage Vfb after receiving the reference signal.

A voltage drop is generated due to the DC resistance of the video signal line 31, and the reference signal and the voltage signal are attenuated. Therefore, the first reference voltage Vref1 in the camera unit 9 changes to the second reference voltage Vref2, and the first voltage Vfb_cis in the camera unit 9 changes to the second voltage Vfb. The value of the second reference voltage Vref2 is less than that of the first reference voltage Vref1. In addition, the value of the second voltage Vfb is less than that of the first voltage Vfb_cis.

It is assumed that the attenuation rate of the reference signal is the same as that of the voltage signal. Therefore, a ratio (Vref1/Vref2) of the value of the first reference voltage Vref1 to the value of the second reference voltage Vref2 is the same as that (Vfb_cis/Vfb) of the value of the first voltage Vfb_cis to the value of the second voltage Vfb.

The AFE 62 includes an analog-to-digital converter and converts the received analog signal into a digital signal. The AFE 62 processes the digital signal of each of the video signal, the reference signal, and the voltage signal. For example, the AFE 62 performs predetermined signal processing on the video signal. In addition, the AFE 62 measures the value of the second reference voltage Vref2 of the received reference signal and measures the value of the second voltage Vfb of the received voltage signal. The AFE 62 outputs the value of the second reference voltage Vref2 and the value of the second voltage Vfb to the correction value calculation circuit 63.

The correction value calculation circuit 63 calculates the value of the second power source voltage Vcis corresponding to the first voltage Vfb_cis by using the value of the first reference voltage Vref1, the value of the second reference voltage Vref2, and the value of the second voltage Vfb. Specifically, the correction value calculation circuit 63 calculates the value of the second power source voltage Vcis by using the value of the first reference voltage Vref1, the value of the second reference voltage Vref2, the value of the second voltage Vfb, and the value of a coefficient k. For example, the correction value calculation circuit 63 calculates the value of the second power source voltage Vcis in accordance with the following Expression (2).

$$Vcis = Vfb\_cis \times k = (Vref1/Vref2) \times Vfb \times k \tag{2}$$

The correction value calculation circuit 63 calculates a control value (correction value) of the first power source voltage Vctrl by using the value of the second power source voltage Vcis. The correction value calculation circuit 63 outputs the calculated control value to the voltage adjustment circuit 64. The voltage adjustment circuit 64 controls the voltage generation circuit 60 based on the control value, thus adjusting the value of the first power source voltage Vctrl to be generated by the voltage generation circuit 60.

The voltage adjustment circuit 64 adjusts the value of the first power source voltage Vctrl such that the value of the second power source voltage Vcis input into the power source terminal 90 is a recommended voltage value for the operation of the imager 94. For example, the recommended voltage value is 3.3 V. In order for the value of the second power source voltage Vcis to be 3.3 V, a condition shown in the following Expression (3) needs to be met.

$$Vctrl(tn)=Vctrl(tn-1)+(3.3-Vcis(tn-1)) \quad (3)$$

A value Vctrl(tn) in Expression (3) indicates the value of the first power source voltage Vctrl at a time point tn. A value Vctrl(tn−1) in Expression (3) indicates the value of the first power source voltage Vctrl at a time point tn−1 before the time point tn. In addition, the value Vctrl(tn−1) indicates the value of the first power source voltage Vctrl adjusted by the voltage adjustment circuit 64 last time. An initial value Vctrl(t0) of the first power source voltage Vctrl at a time point t0 is a predetermined value. A value Vcis(tn−1) in Expression (3) indicates the value of the second power source voltage Vcis at the time point tn−1. The correction value calculation circuit 63 calculates the value Vctrl(tn) of the first power source voltage Vctrl in accordance with Expression (3) and outputs the value Vctrl(tn) to the voltage adjustment circuit 64.

When the amount of the voltage drop in the power source line 30 becomes large, the value of the second power source voltage Vcis becomes small. Therefore, the voltage adjustment circuit 64 increases the value of the first power source voltage Vctrl. When the amount of the voltage drop in the power source line 30 becomes small, the value of the second power source voltage Vcis becomes large. Therefore, the voltage adjustment circuit 64 decreases the value of the first power source voltage Vctrl.

In the first embodiment, the endoscope system 1 can monitor the power source voltage (second power source voltage Vcis) provided to the imager 94. The video signal line 31 transfers the reference signal and the voltage signal used for adjusting the value of the first power source voltage Vctrl. Therefore, a dedicated cable used for transferring the reference signal and the voltage signal is unnecessary, and miniaturization of the camera unit 9 is not prevented.

The endoscope system 1 calculates the value of the second power source voltage Vcis based on a relationship of the amount between the first reference voltage Vref1 having a known value and the second reference voltage Vref2 that has been attenuated in the video signal line 31. Therefore, the endoscope system 1 can calculate the value of the second power source voltage Vcis based on an analog signal with high accuracy.

Since the AFE 62 that processes the video signal measures the value of the second reference voltage Vref2 and the value of the second voltage Vfb, an increase of the circuit scale is restricted. The endoscope system 1 can adjust the value of the first power source voltage Vctrl by following a change of the voltage drop in the power source line 30.

Second Embodiment

Figure 5:
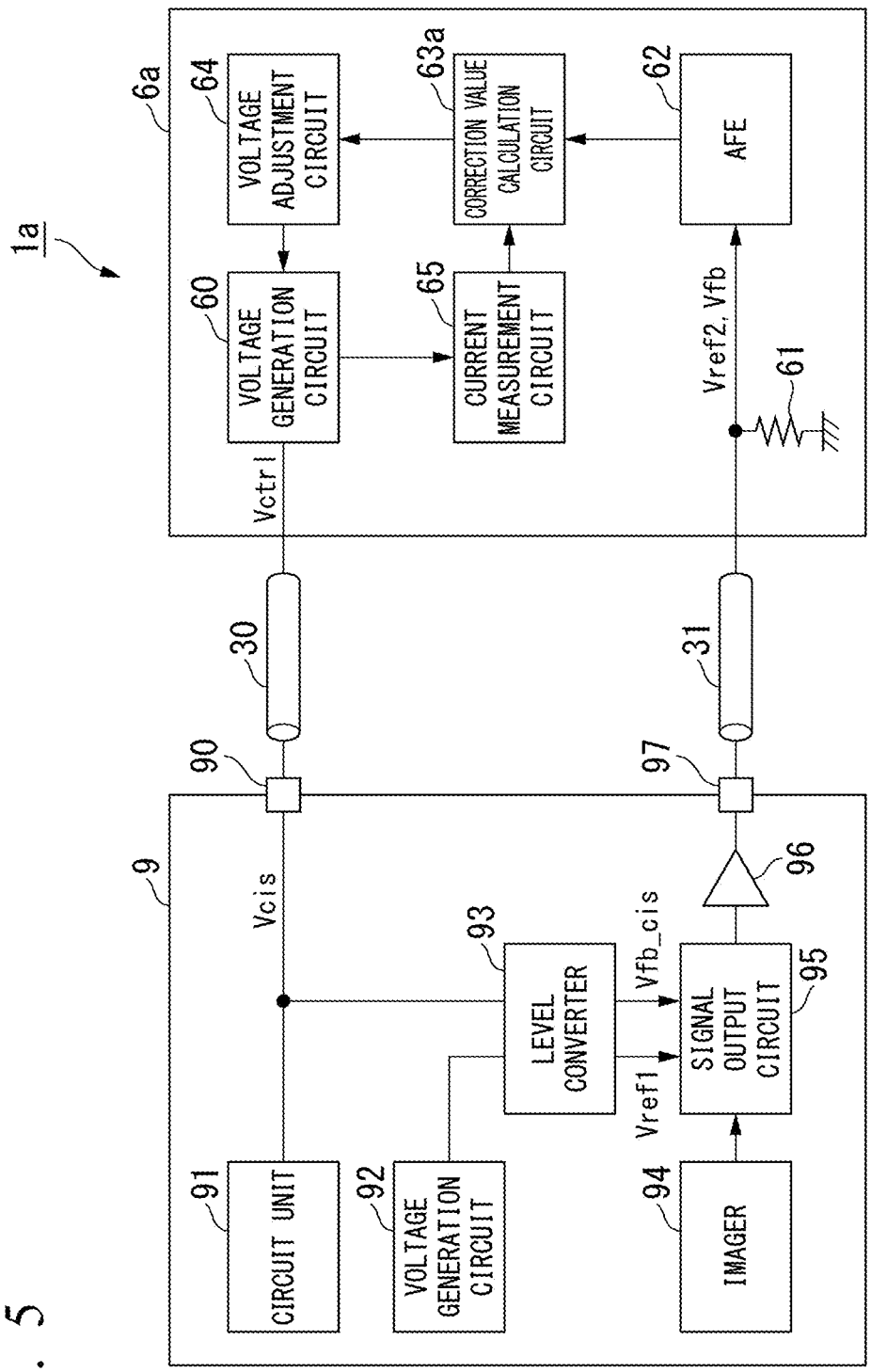
FIG. 5 is a block diagram showing a configuration of an endoscope system according to a second embodiment of the present invention.

FIG. 5 shows an internal configuration of an endoscope system 1a according to a second embodiment of the present invention. The same configuration as that shown in FIG. 2 will not be described. The endoscope system 1a shown in FIG. 5 includes a camera unit 9 and a processor 6a.

The camera unit 9 is the same as that shown in FIG. 2. The processor 6a includes a voltage generation circuit 60, a resistor 61, an AFE 62, a correction value calculation circuit 63a, a voltage adjustment circuit 64, and a current measurement circuit 65. All or part of the configuration of the processor 6a shown in FIG. 5 may be disposed in the operation unit 4 or the connector unit 5.

The current measurement circuit 65 measures a value of a current (DC current) that flows through the power source line 30. The current measurement circuit 65 outputs the measured value to the correction value calculation circuit 63a.

The correction value calculation circuit 63a calculates a resistance value Rvdd(tn−1) of the power source line 30 at a time point tn−1 by using a value Vctrl(tn−1) of the first power source voltage Vctrl at the time point tn−1, a value Vcis(tn−1) of the second power source voltage Vcis at the time point tn−1, and a value Ivdd(tn−1) of the current at the time point tn−1. For example, the correction value calculation circuit 63a can calculate the resistance value Rvdd(tn−1) in accordance with the following Expression (4).

$$Rvdd(tn-1)=(Vctrl(tn-1)-Vcis(tn-1)/Ivdd(tn-1) \quad (4)$$

The value Vctrl(tn) of the first power source voltage Vctrl at a time point tn, the value Vcis(tn−1) of the second power source voltage Vcis at the time point tn−1, the resistance value Rvdd(tn−1) of the power source line 30 at the time point tn−1, and the value Ivdd(tn−1) of the current at the time point tn−1 meet a condition shown in the following Expression (5).

$$Vcis(tn-1)=Vctrl(tn)-(Rvdd(tn-1)\times Ivdd(tn-1)) \quad (5)$$

Accordingly, in order for the value of the second power source voltage Vcis to be 3.3 V, a condition shown in the following Expression (6) needs to be met.

$$Vctrl(tn)=3.3+(Rvdd(tn-1)\times Ivdd(tn-1)) \quad (6)$$

The correction value calculation circuit 63a calculates the value Vctrl(tn) of the first power source voltage Vctrl in accordance with Expression (6) and outputs the value Vctrl (tn) to the voltage adjustment circuit 64. The voltage adjustment circuit 64 controls the voltage generation circuit 60 based on the value Vctrl(tn).

In the second embodiment, the endoscope system 1a can monitor the power source voltage provided to the imager 94 and does not prevent miniaturization of the camera unit 9 similarly to the endoscope system 1 according to the first embodiment. In addition, the endoscope system 1a can calculate the resistance value of the power source line 30 and can calculate the amount of the voltage drop in the power source line 30. The endoscope system 1a controls the voltage generation circuit 60 based on the amount and therefore can directly adjust the value of the first power source voltage to be generated by the voltage generation circuit 60.

Third Embodiment

Figure 6:
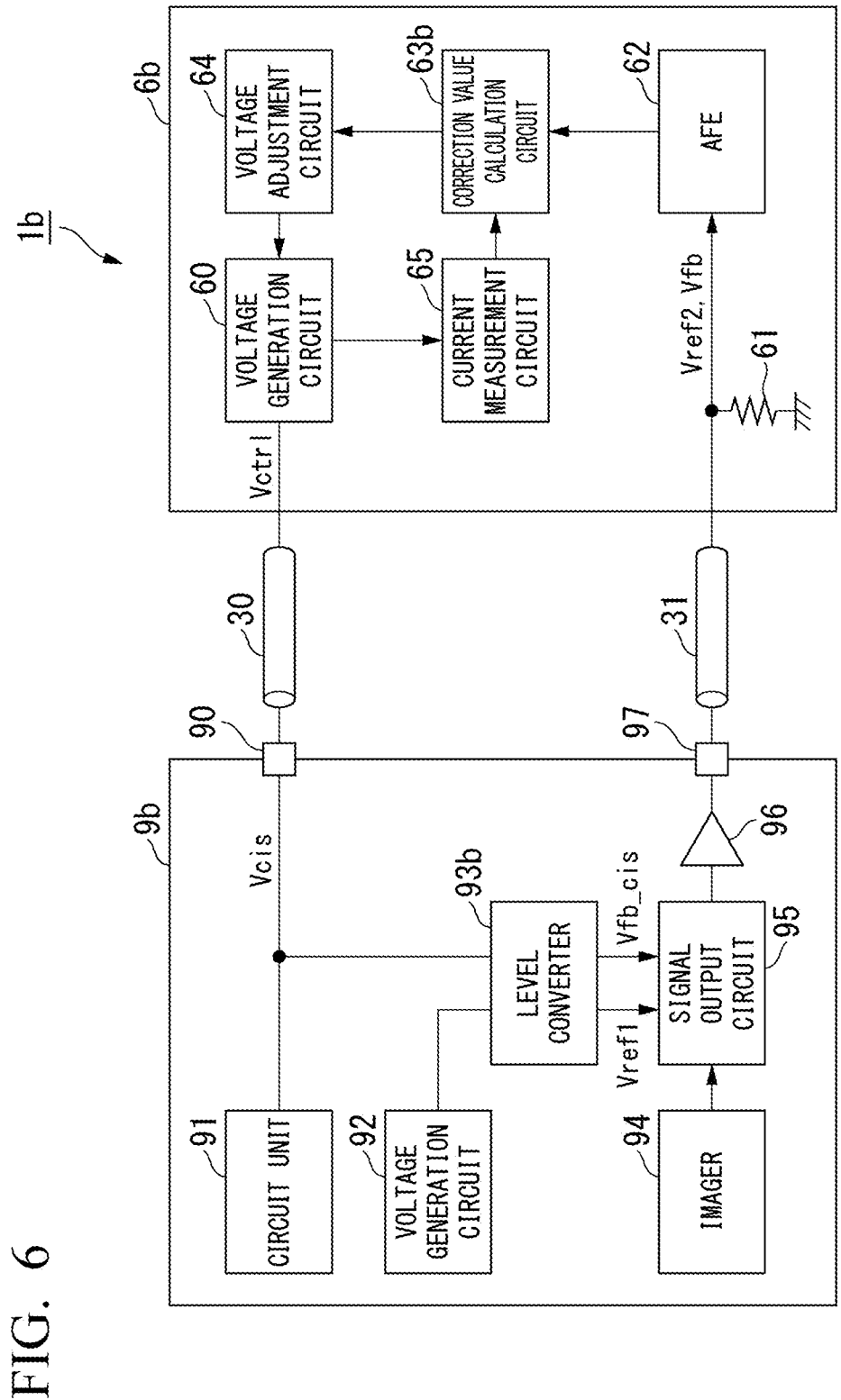
FIG. 6 is a block diagram showing a configuration of an endoscope system according to a third embodiment of the present invention.

FIG. 6 shows an internal configuration of an endoscope system 1b according to a third embodiment of the present invention. The same configuration as that shown in FIG. 5 will not be described. The endoscope system 1b shown in FIG. 6 includes a camera unit 9b and a processor 6b.

The camera unit 9b includes a power source terminal 90, a circuit unit 91, a voltage generation circuit 92, a level converter 93b, an imager 94, a signal output circuit 95, a buffer 96, and a video terminal 97. At least one of the circuit unit 91, the voltage generation circuit 92, the level converter 93b, the signal output circuit 95, and the buffer 96 may be disposed in the imager 94.

The processor 6b includes a voltage generation circuit 60, a resistor 61, an AFE 62, a correction value calculation circuit 63b, a voltage adjustment circuit 64, and a current measurement circuit 65. All or part of the configuration of the processor 6b shown in FIG. 6 may be disposed in the operation unit 4 or the connector unit 5.

The level converter 93b converts the second power source voltage Vcis into a first voltage Vfb_cis. Specifically, the level converter 93b converts the second power source voltage Vcis into a first voltage Vcis/m and a first voltage Vcis/n. Each of a coefficient m and a coefficient n is a predetermined value greater than 1. Each of the coefficient m and the coefficient n indicates a ratio of the value of the second power source voltage Vcis to the value of the first voltage. The value of the first voltage Vcis/m and the value of the first voltage Vcis/n are less than the value of the second power source voltage Vcis. For example, the value of the coefficient n is greater than that of the coefficient m, and the value of the first voltage Vcis/n is less than that of the first voltage Vcis/m. The first voltage Vfb_cis indicates the difference between the first voltage Vcis/m and the first voltage Vcis/n.

On the other hand, the level converter 93b converts the first reference voltage generated by the voltage generation circuit 92 into a first reference voltage Vref1, thus generating a reference signal. The first reference voltage Vref1 indicates the difference between a predetermined voltage Vbgr and the first voltage Vcis/n. The level converter 93b outputs the first reference signal having the first reference voltage Vref1 and a voltage signal having the first voltage Vfb_cis to the signal output circuit 95.

The signal output circuit 95 outputs the video signal output from the imager 94 to the video signal line 31 in a first period. The signal output circuit 95 outputs the reference signal output from the level converter 93b to the video signal line 31 in a second period different from the first period. The signal output circuit 95 outputs the voltage signal output from the level converter 93b to the video signal line 31 in a third period different from any of the first period and the second period.

The AFE 62 receives the video signal, the reference signal, and the voltage signal and measures a value of the second reference voltage Vref2 and a value of the second voltage Vfb. The AFE 62 outputs the value of the second reference voltage Vref2 and the value of the second voltage Vfb to the correction value calculation circuit 63b. The current measurement circuit 65 measures a value of a current that flows through the power source line 30 and outputs the measured value to the correction value calculation circuit 63b.

The correction value calculation circuit 63b determines whether the value of the second voltage Vfb is the same as that of the second reference voltage Vref2. When the value of the second voltage Vfb is the same as that of the second reference voltage Vref2, the correction value calculation circuit 63b calculates the resistance value of the power source line 30 by using the value of the first power source voltage Vctrl, the value of the first reference voltage Vref1, and the value of the current. The correction value calculation circuit 63b calculates a control value of the first power source voltage Vctrl by using the calculated resistance value. The correction value calculation circuit 63b outputs the calculated control value to the voltage adjustment circuit 64. The voltage adjustment circuit 64 controls the voltage generation circuit 60 based on the control value, thus adjusting the value of the first power source voltage Vctrl to be generated by the voltage generation circuit 60.

When the value of the second voltage Vfb is the same as that of the second reference voltage Vref2, the second power source voltage Vcis has a value that is based on the value of the first reference voltage Vref1 and the coefficient m. A method of acquiring the value of the second power source voltage Vcis will be described by using FIGS. 7 to 12.

Figure 7:
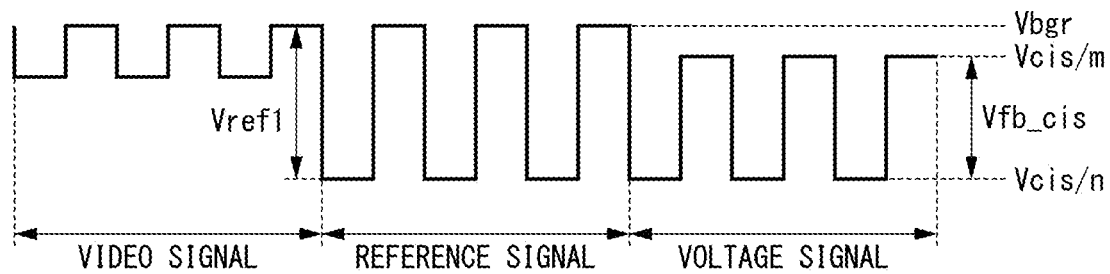
FIG. 7 is a timing chart showing a waveform of each signal output from a signal output circuit included in the endoscope system according to the third embodiment of the present invention.
Figure 8:
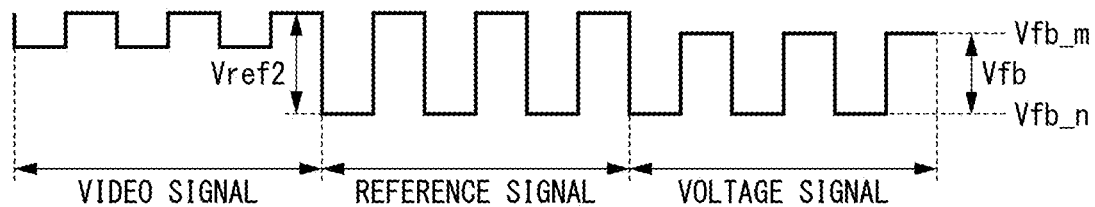
FIG. 8 is a timing chart showing a waveform of each signal received by a signal reception circuit included in the endoscope system according to the third embodiment of the present invention.
Figure 9:
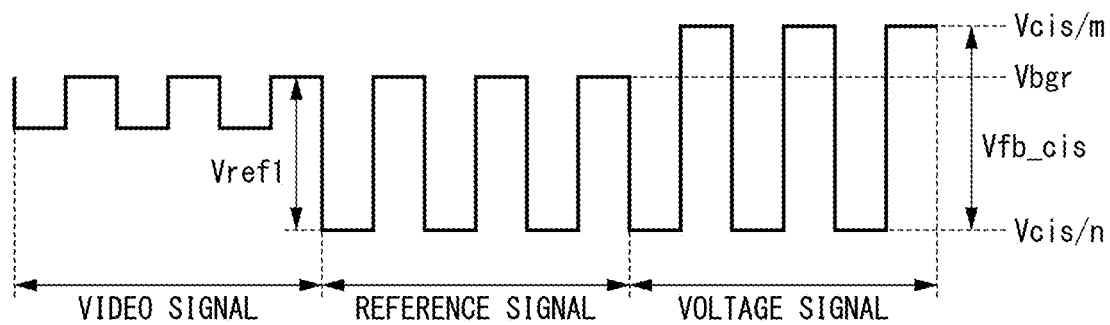
FIG. 9 is a timing chart showing a waveform of each signal output from the signal output circuit included in the endoscope system according to the third embodiment of the present invention.
Figure 10:
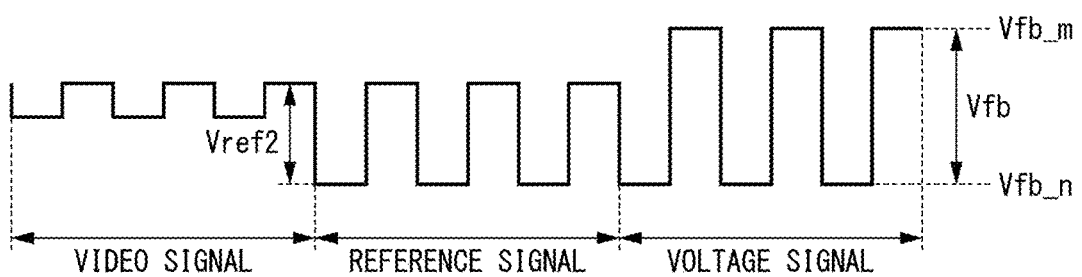
FIG. 10 is a timing chart showing a waveform of each signal received by the signal reception circuit included in the endoscope system according to the third embodiment of the present invention.
Figure 11:
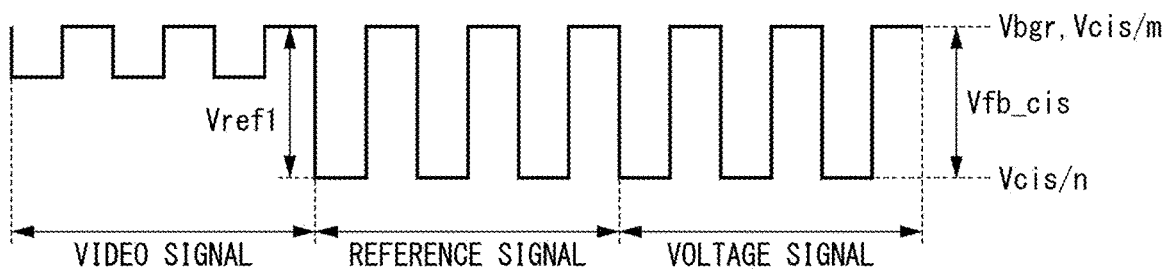
FIG. 11 is a timing chart showing a waveform of each signal output from the signal output circuit included in the endoscope system according to the third embodiment of the present invention.
Figure 12:
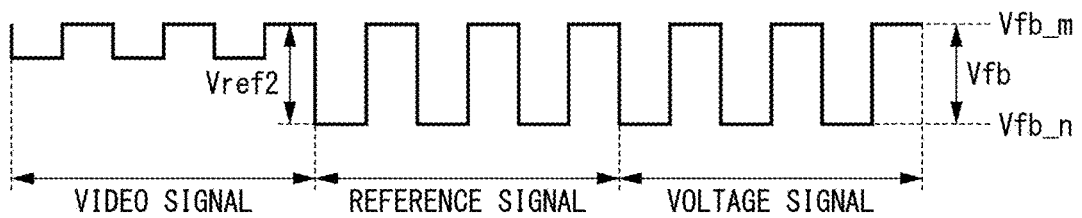
FIG. 12 is a timing chart showing a waveform of each signal received by the signal reception circuit included in the endoscope system according to the third embodiment of the present invention.

FIGS. 7, 9, and 11 show a waveform of each signal output from the signal output circuit 95. FIGS. 8, 10, and 12 show a waveform of each signal received by the AFE 62, which is a signal reception circuit. Waveforms of the video signal, the reference signal, and the voltage signal are shown in each drawing. The horizontal direction in each drawing indicates time, and the vertical direction in each drawing indicates a voltage value.

A voltage drop is generated due to the DC resistance of the video signal line 31, and the reference signal and the voltage signal are attenuated. Therefore, the first reference voltage Vref1 in the camera unit 9b changes to the second reference voltage Vref2. The value of the second reference voltage Vref2 is less than that of the first reference voltage Vref1. In addition, the first voltage Vcis/m in the camera unit 9b changes to a second voltage Vfb_m, and the first voltage Vcis/n in the camera unit 9b changes to a second voltage Vfb_n. The second voltage Vfb indicates the difference between the second voltage Vfb_m and the second voltage Vfb_n. The value of the second voltage Vfb is less than that of the first voltage Vfb_cis.

FIG. 7 shows an example in which the value of the first voltage Vfb_cis is less than that of the first reference voltage Vref1. In this case, the value of the second voltage Vfb is less than that of the second reference voltage Vref2 as shown in FIG. 8.

FIG. 9 shows an example in which the value of the first voltage Vfb_cis is greater than that of the first reference voltage Vref1. In this case, the value of the second voltage Vfb is greater than that of the second reference voltage Vref2 as shown in FIG. 10.

In the examples shown in FIG. 8 and FIG. 10, the value of the second voltage Vfb is different from that of the second reference voltage Vref2. The correction value calculation circuit 63b outputs the control value of the first power source voltage Vctrl causing the value of the second voltage Vfb to match the value of the second reference voltage Vref2 to the voltage adjustment circuit 64.

For example, when the value of the second voltage Vfb is less than that of the second reference voltage Vref2, the correction value calculation circuit 63b outputs the control value to increase the value of the first power source voltage Vctrl to the voltage adjustment circuit 64. When the value of the second voltage Vfb is greater than that of the second reference voltage Vref2, the correction value calculation circuit 63b outputs the control value to decrease the value of the first power source voltage Vctrl to the voltage adjustment circuit 64.

The voltage adjustment circuit 64 controls the voltage generation circuit 60 based on the control value, thus adjusting the value of the first power source voltage Vctrl to be generated by the voltage generation circuit 60. The above-described control is repeated until the value of the second voltage Vfb matches the value of the second reference voltage Vref2.

FIG. 11 shows an example in which the value of the first voltage Vfb_cis is the same as that of the first reference voltage Vref1. In this case, the value of the second voltage Vfb is the same as that of the second reference voltage Vref2 as shown in FIG. 12.

When the value of the second voltage Vfb is the same as that of the second reference voltage Vref2, the value of the first voltage Vfb_cis is the same as that of the first reference voltage Vref1 and the value of the first voltage Vcis/m is the same as that of the predetermined voltage Vbgr. Therefore, the value of the second power source voltage Vcis meets a condition shown in the following Expression (7). The correction value calculation circuit 63b can acquire the value of the second power source voltage Vcis shown in Expression (7).

$$Vcis=Vbgr \times m \qquad (7)$$

When the value of the second voltage Vfb at a time point tn−1 is the same as that of the second reference voltage Vref2 at the time point tn−1, the correction value calculation circuit 63b calculates a resistance value Rvdd(tn−1) of the power source line 30 at the time point tn−1 by using a value Vctrl(tn−1) of the first power source voltage Vctrl at the time point tn−1, a value Vcis(tn−1) of the second power source voltage Vcis at the time point tn−1, and a value Ivdd(tn−1) of the current at the time point tn−1. For example, the correction value calculation circuit 63b can calculate the resistance value Rvdd(tn−1) in accordance with Expression (4) described above.

The correction value calculation circuit 63b calculates a value Vctrl(tn) of the first power source voltage Vctrl in accordance with Expression (6) described above by using the resistance value Rvdd(tn−1) and the value Ivdd(tn−1) at the time point tn−1. The correction value calculation circuit 63b outputs the calculated value Vctrl(tn) to the voltage adjustment circuit 64. The voltage adjustment circuit 64 controls the voltage generation circuit 60 based on the value Vctrl(tn).

In the third embodiment, the endoscope system 1b can monitor the power source voltage provided to the imager 94 and does not prevent miniaturization of the camera unit 9b similarly to the endoscope system 1 according to the first embodiment. When the value of the second voltage Vfb matches the value of the second reference voltage Vref2, the endoscope system 1b can calculate the resistance value of the power source line 30 and can calculate the amount of the voltage drop in the power source line 30. The endoscope system 1b controls the voltage generation circuit 60 based on the amount and therefore can directly adjust the value of the first power source voltage to be generated by the voltage generation circuit 60.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device, comprising:
    a camera unit including:
        an image sensor configured to receive a first power source voltage transferred by a power source line as a second power source voltage and generate a video signal by using the second power source voltage;
        a reference voltage generation circuit configured to generate a first reference voltage; and
        a signal output circuit configured to output the video signal, a reference signal having the first reference voltage, and a voltage signal having a first voltage indicating the second power source voltage to a video signal line; and
    a control unit including:
        a signal reception circuit configured to receive the video signal transferred by the video signal line, the reference signal having a second reference voltage, and the voltage signal having a second voltage and measure a value of the second reference voltage and a value of the second voltage,
            wherein the received reference signal has the second reference voltage that has changed from the first reference voltage, and
            wherein the received voltage signal has the second voltage that has changed from the first voltage;
        a calculation circuit configured to calculate a control value used for adjusting a value of the first power source voltage by using a value of the first reference voltage, the value of the second reference voltage, and the value of the second voltage;
        a power source voltage generation circuit configured to generate the first power source voltage and output the generated first power source voltage to the power source line; and
        a voltage adjustment circuit configured to adjust the value of the first power source voltage by controlling the power source voltage generation circuit based on the control value.

2. The imaging device according to claim 1,
    wherein the control unit further includes a current measurement circuit configured to measure a value of a current that flows through the power source line, and
    wherein the calculation circuit is configured to calculate a resistance value of the power source line by using the value of the first power source voltage, the value of the first reference voltage, and the value of the current and calculate the control value by using the resistance value when the value of the second voltage is the same as the value of the second reference voltage.

3. The imaging device according to claim 2,
    wherein a value of the second power source voltage is not within a range of a voltage of the video signal,
    wherein the camera unit further includes a conversion circuit configured to convert the second power source voltage into the first voltage having a value within the range so as to generate the voltage signal, and
    wherein the calculation circuit is configured to calculate the resistance value by using the value of the first power source voltage, the value of the first reference voltage, the value of the current, and a value indicating a ratio of the value of the second power source voltage to the value of the first voltage.

4. The imaging device according to claim 1,
    wherein the calculation circuit is configured to calculate a value of the second power source voltage corresponding to the first voltage by using the value of the first reference voltage, the value of the second reference voltage, and the value of the second voltage and calculate the control value by using the value of the second power source voltage.

5. The imaging device according to claim 4,
    wherein a value of the second power source voltage is not within a range of a voltage of the video signal,
    wherein the camera unit further includes a conversion circuit configured to convert the second power source voltage into the first voltage having a value within the range so as to generate the voltage signal, and
    wherein the calculation circuit is configured to calculate the value of the second power source voltage by using the value of the first reference voltage, the value of the second reference voltage, the value of the second voltage, and a value indicating a ratio of the value of the second power source voltage to the value of the first voltage.

6. The imaging device according to claim 4,
wherein the control unit further includes a current measurement circuit configured to measure a value of a current that flows through the power source line, and
wherein the calculation circuit is configured to calculate a resistance value of the power source line by using the value of the first power source voltage, the value of the second power source voltage, and the value of the current and calculate the control value by using the resistance value.

7. The imaging device according to claim 1,
wherein the signal output circuit is configured to output the video signal to the video signal line in a first period, output the reference signal to the video signal line in a second period different from the first period, and output the voltage signal to the video signal line in a third period different from any of the first period and the second period.

8. An endoscope system, comprising:
a scope that has a distal end and is to be inserted into a living body; and
the imaging device according to claim 1,
wherein the camera unit is disposed in the distal end.

9. An imaging method, comprising:
receiving a first power source voltage transferred by a power source line as a second power source voltage;
generating a video signal by using the second power source voltage;
generating a first reference voltage;
outputting the video signal, a reference signal having the first reference voltage, and a voltage signal having a first voltage indicating the second power source voltage to a video signal line;
receiving the video signal transferred by the video signal line, the reference signal having a second reference voltage, and the voltage signal having a second voltage,
wherein the received reference signal has the second reference voltage that has changed from the first reference voltage, and
wherein the received voltage signal has the second voltage that has changed from the first voltage;
measuring a value of the second reference voltage and a value of the second voltage;
calculating a control value used for adjusting a value of the first power source voltage by using a value of the first reference voltage, the value of the second reference voltage, and the value of the second voltage;
generating the first power source voltage;
outputting the generated first power source voltage to the power source line; and
adjusting the value of the first power source voltage by controlling a power source voltage generation circuit based on the control value.

* * * * *